United States Patent [19]

Birch et al.

[11] Patent Number: 5,597,463

[45] Date of Patent: Jan. 28, 1997

[54] DEVICE FOR ELECTROCHEMICAL MEASUREMENTS

[75] Inventors: Brian J. Birch, Chelveston; Nicholas A. Morris, Kempston, both of United Kingdom

[73] Assignee: Van den Bergh Foods Co., Division of Conopco, Inc., Lisle, Ill.

[21] Appl. No.: 476,774

[22] Filed: Jun. 7, 1995

[30] Foreign Application Priority Data

Jul. 5, 1994 [GB] United Kingdom ............... 9413525

[51] Int. Cl.⁶ .................................................. G01N 27/26
[52] U.S. Cl. ........................... 204/405; 204/412; 204/433; 205/787.5; 205/788
[58] Field of Search ............................... 204/153.23, 405, 204/416, 418, 419, 412, 433; 205/787.5, 788

[56] References Cited

U.S. PATENT DOCUMENTS

| 3,131,133 | 4/1964 | Barendrecht | 204/405 |
| 3,162,585 | 12/1964 | De Ford et al. | 204/405 |
| 3,441,490 | 4/1969 | Johansson | 204/405 |
| 3,498,888 | 3/1970 | Johansson | 204/405 |
| 3,563,875 | 2/1971 | Coulson | 204/405 |
| 3,716,334 | 2/1973 | Pont | 204/405 |
| 4,534,356 | 8/1985 | Papadakis | 204/403 |
| 4,915,812 | 4/1990 | Parce et al. | 204/403 |
| 4,966,671 | 10/1990 | Nylander et al. | 204/153.14 |
| 5,041,202 | 8/1991 | Friconneau et al. | 204/405 |

FOREIGN PATENT DOCUMENTS

| 023156 | 1/1981 | European Pat. Off. . |
| 138152 | 4/1985 | European Pat. Off. . |
| 170375 | 2/1986 | European Pat. Off. . |
| 326421 | 8/1989 | European Pat. Off. . |
| 569908A2 | 11/1993 | European Pat. Off. . |

OTHER PUBLICATIONS

Sensors and Actuators, Olthuis W., B.7 (1992)month unavailable, Nos. 1/3. pp. 479–483, "Simplified design of the coulometric sensor–actuator system by the application of a time dependent acutuator current".

Primary Examiner—T. Tung
Attorney, Agent, or Firm—Gerard J. McGowan, Jr.

[57] ABSTRACT

A titration electrode device for measuring the amount of a species in solution in a test liquid comprises a counter electrode and a generator electrode both in a chamber for receiving a thin layer of test liquid, the two electrodes being located in respective compartments within the chamber such that ionic conduction between the compartments is permitted but diffusion of electrogenerated reagents between the compartments is restricted, the device including reference and sensor electrodes in the chamber.

12 Claims, 3 Drawing Sheets

DEVICE FOR ELECTROCHEMICAL MEASUREMENTS

FIELD OF INVENTION

This invention relates to electrochemical measurements, and particularly concerns titration electrode devices.

SUMMARY OF THE INVENTION

According to one aspect of the present invention there is provided a titration electrode device for measuring the amount of a species in solution in a test liquid, comprising a counter electrode and a generator electrode both in a chamber for receiving a thin layer of test liquid, the two electrodes being located in respective compartments within the chamber such that ionic conduction between the compartments is permitted but diffusion of electrogenerated reagents between the compartments is restricted, the device including reference and sensor electrodes in the chamber.

The counter electrode and generator electrode function together in use, being electrically connected by external conductors and also ionically connected via the test liquid, and act to generate a localised ionic environment, e.g. of $H^+$ or $OH^-$, at the generator electrode, with the complementary ion, e.g. $OH^-$ or $H^+$, generated at the counter electrode. The ions generated at the generator electrode react, directly or indirectly, with the species in solution to be measured. The sensor electrode detects local changes in ionic concentration in the vicinity of the generator electrode by measuring the potential difference between the sensor electrode and the reference electrode, with the reference electrode functioning to provide a stable arbitrary potential relative to the sensor electrode.

In use, a test liquid is introduced to the chamber and a low impedance circuit is set up between the counter electrode and generator electrode to generate the localised ionic environment in the vicinity of the generator electrode, as describe in International Publication No. WO 94/15207. Depending on the nature of the test liquid, it may be necessary to include an electrochemically inert salt in the chamber, e.g. by depositing a salt such as potassium sulphate, potassium chloride, sodium nitrate, etc, as described in WO 94/15207. Simultaneously, a high impedance circuit is set up between the sensor electrode and reference electrode, and the potential difference between the reference and sensor electrodes is measured over time. The time taken to reach equivalence is determined, from which can be calculated the amount of species of interest present in the test liquid.

The device of the invention will generally be used for measuring the amount of ionic species in solution, but may in appropriate conditions also be used to measure non-ionic species, such as water in a Karl Fisher reaction, or quinones.

The term "thin layer" is used to mean having a thickness less than 1 mm, conveniently in the range 0.1 to 0.2 mm. The device of the invention can thus conveniently be embodied in the form of a so-called capillary fill device (CFD), e.g. as disclosed in EP 0170375A.

References to restricted diffusion mean restricted over the timescale in which titration measurements are typically carried out using the device of the invention. In practice timescales of 60 to 400 sec are typical.

The separate compartments for the electrodes are conveniently produced by having physical barriers that define the compartments within the chamber, while nevertheless permitting some fluid communication between the compartments. One preferred embodiment, in the form of a CFD, comprises two parallel plates supported by side walls at a distance of less than 1 mm to form an open ended chamber for receiving a sample. The chamber is internally divided by ridges extending parallel to the side walls, to define open-ended, side-by-side compartments. The ridges do not extend along the full length of the chamber, so that ionic communication between the compartments is permitted. Electrodes are located within the compartments, the intervening ridges acting to restrict inter-compartmental diffusion of electrogenerated species. For ease of manufacture, the electrodes are preferably located, e.g. screen printed, on one plate, e.g. a bottom plate, with the ridges being formed on the other plate, e.g. a top plate.

A separate reference electrode may be provided, located in a separate compartment within the chamber, e.g. located between the other two compartments. Alternatively, the function of the reference electrode may additionally be performed by the counter electrode.

A separate sensor electrode may be provided, in the vicinity of the generator electrode and in the same compartment therewith. Alternatively, the function of the sensor electrode may additionally be performed by the generator electrode.

In the simplest case, the device thus comprises two electrodes, each performing a dual function: a counter/reference electrode, and a generator/sensor electrode. In use, the two electrodes are connected via a high impedance circuit and a low impedance circuit, as described above. Such an embodiment is very simple to fabricate and is amenable to mass manufacture.

In a further aspect the present invention thus provides a titration electrode device for measuring the amount of a species in solution in a test liquid, comprising a counter electrode and a generator electrode both in a chamber for receiving a thin layer of test liquid, the device including reference and sensor electrodes in the chamber, wherein the counter electrode additionally performs the function of the reference electrode and/or the generator electrode additionally performs the function of the sensor electrode.

The two aspects of the invention may be used separately or in combination.

The reagent generated at the generator electrode may comprise hydrogen ions or hydroxyl ions, which are readily produced by application of an electrical potential to water as described in WO 94/15207. Other reagents such as chlorine, bromine and iodine, can alternatively be produced by treatment of suitable salt solutions, e.g. to KCl, KBr, KI. The reagent generated will be selected having regard to the species in solution to be measured. In the simplest case, a constant current is applied between the counter and generator electrodes. The current will be selected depending on factors including the likely amount of species to be measured and intended timescale of the test. A current in the range 5 to 30 μA will typically be appropriate. Instead of a constant current it is generally preferable to apply a varying current under suitable software control for improved resolution.

The counter and generator electrodes preferably comprise a noble metal e.g. palladium. The sensor electrode may also comprise palladium, although other pH electrodes such as ruthenium oxide and iridium oxide may be used. The reference electrode conveniently comprises a silver/silver chloride electrode, although other reference systems may alternatively be used.

The electrodes and associated connectors are preferably formed by a screen printing process, which lends itself well to mass manufacture of the devices.

The invention finds particular application as an acid titration device for measuring the acid content of fruit, e.g. tomatoes, to provide an indication of ripeness and hence readiness for picking. Such a device conveniently incorporates further electrodes for measuring reducing sugars, as described in International Application No. PCT/GB94/02656, to provide further information on fruit ripeness.

The presence of compartments in the device may be exploited by creating different chemical environments in different compartments. For example, different chemical reagents may be generated in situ as described in WO 94/15207 in different compartments and/or different chemical reagents may be deposited in different compartments.

The invention will be further described, by way of illustration, with reference to the accompanying drawings, in which.

DETAILED DESCRIPTION OF THE DRAWINGS

Figure 1:
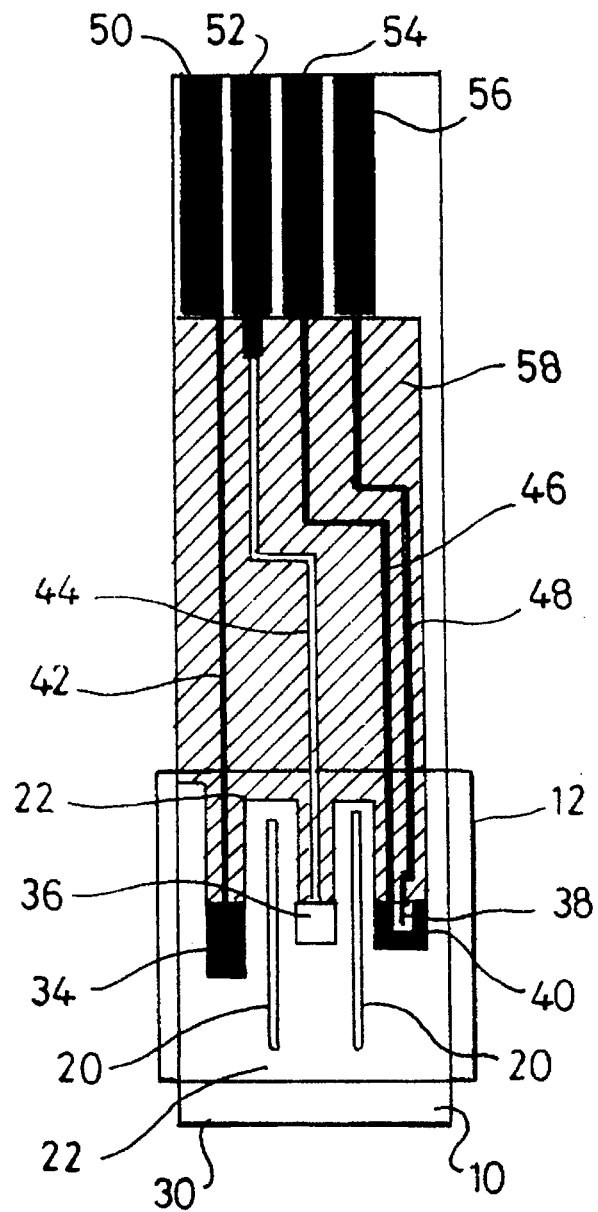
FIG. 1 is a plan view of a device in accordance with the invention.
Figure 2:
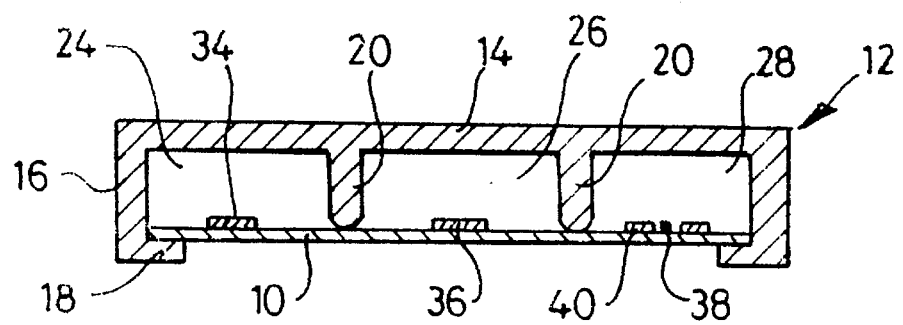
FIG. 2 is a schematic sectional view, to an enlarged scale, of the device of FIG. 1.

The device illustrated in FIGS. 1 and 2 is a titration device, designed to measure the amount of acid or alkali present in a test liquid. The device comprises a rectangular, planar bottom plate 10 made of rigid plastics or ceramic material, and a top plate 12 of injection moulded polycarbonate. Top plate 12 has a rectangular planar upper face 14 with two side limbs 16 terminating in inwardly turned lips 18. The top plate 12 is dimensional to receive the bottom plate 10 with a tight friction fit. Two parallel elongate ridges 20 extend inwardly from the top plate upper face, to engage the bottom face, running parallel to the side limbs 16. The ridges 20 do not extend along the full length of upper face 14, but terminate short of the plate edges, leaving a small gap 22 (3 mm long) at each end. The plates thus define therebetween a sample receiving region that is divided into separate compartments 24, 26 and 28 by the ridges.

The bottom plate has a length of about 5 cm and a width of about 1.5 cm. Top plate has a length of about 1.4 cm and a width of about 1.8 cm, and is positioned relative to the bottom plate to leave a protruding, sample-receiving lip 30 about 0.2 cm in length. The bottom plate and the upper face of the top plate are separated by a gap of about 100 μ(0.1 mm) which is sufficiently small that liquid can be drawn into the sample-receiving region via the lip, by capillary action.

The upper face of the bottom plate 10 bears a series of electrodes, located within the compartments: a palladium counter electrode 34 is located in compartment 24, a silver/silver chloride reference electrode 36 is located in compartment 26 and a palladium sensor electrode 38 with surrounding palladium generator electrode 40 are located in compartment 28. Conductive tracks 42, 44, 46 and 48 lead from the electrodes to respective palladium connectors 50, 52, 54 and 56 at the opposed end of plate 10, for appropriate electrical connection. The electrodes, conductive tracks and connectors are deposited using conventional screen printing techniques. Conducting polymer inks such as are used in the thick film industry, e.g. comprising palladium in a standard vehicle, are screen printed, dried and fired in accordance with manufacturers instructions.

A layer of dielectric material 58 is deposited, e.g. by printing, over the tracks 42, 44, 46 and 48 as shown.

In use, a liquid to be tested, to measure the amount of acid or alkali present, is located on sample-receiving lip 30, from where it is drawn into the 3 sample-receiving compartments 24, 26 and 28 by capillary action. The ridges 20 separate the 3 compartments in such a way that ionic conduction between the compartments is permitted by means of flow of ions through the gaps 22 at the end of the ridges 20, but diffusion between compartments of reagents generated electrochemically during use of the device is prevented within the timescale of the test by the physical barrier constituted by the ridges: the path length between compartments, around a ridge and through a gap, is longer than can be traversed in the duration of a typical test. In this way the reagents in the 3 compartments are effectively separated from each other, while the compartments are nevertheless in ionic connection.

Depending on the ionic strength of the sample it may be necessary or preferable to add electrochemically inert salt such as potassium nitrate, potassium sulphate or potassium chloride to the system. The salt may either be added to the sample in appropriate amount or may be deposited within the compartments, e.g. by being evaporated from solution, screen printed using a suitable vehicle, or by ink jet printing, to adhere to an internal major face of the chamber, e.g. top plate 12 and/or bottom plate 10. The salt is present for the purposes of ionic conduction, and concentrations of up to about 1M may typically be used.

A low impedance circuit (not shown) is set up between counter electrode 34 and generator electrode 40 via connectors 50 and 54. This functions to generate a localised environment consisting of $OH^-$ or $H^+$, by the process described in WO 94/15207, in the vicinity of sensor electrode 38. Where the device is to be used to measure the amount of acid present in a sample, this circuit is set up to generate $OH^-$ at the generator electrode. This reacts with $H^+$ in the sample, producing local changes in $H^+$ concentration and thereby changes in potential difference (redox potential) in the vicinity of the sensor electrode. The opposite applies for measuring $OH^-$.

Such changes are measured by simultaneously setting up a high impedance potentiometric circuit (not shown) between the sensor electrode 40 and the reference electrode 38, via connectors 56 and 52. The reference electrode provides a stable, arbitrary redox potential relative to the sensor electrode, to measure changes in $H^+$ (or $OH^-$) at the sensor electrode.

The potential difference (redox potential) between the reference and sensor electrodes is measured, and a plot of potential in volts versus time gives a characteristic sigmoidal curve, with the point of inflection indicating the point of equivalence (neutrality). The time taken to reach equivalence thus provides an indication of the amount of acid (or alkali) in the sample.

Computer control means and measurement means (not shown) are used to control and monitor functioning of the device using conventional techniques as are well known to those skilled in the field.

Figure 3:
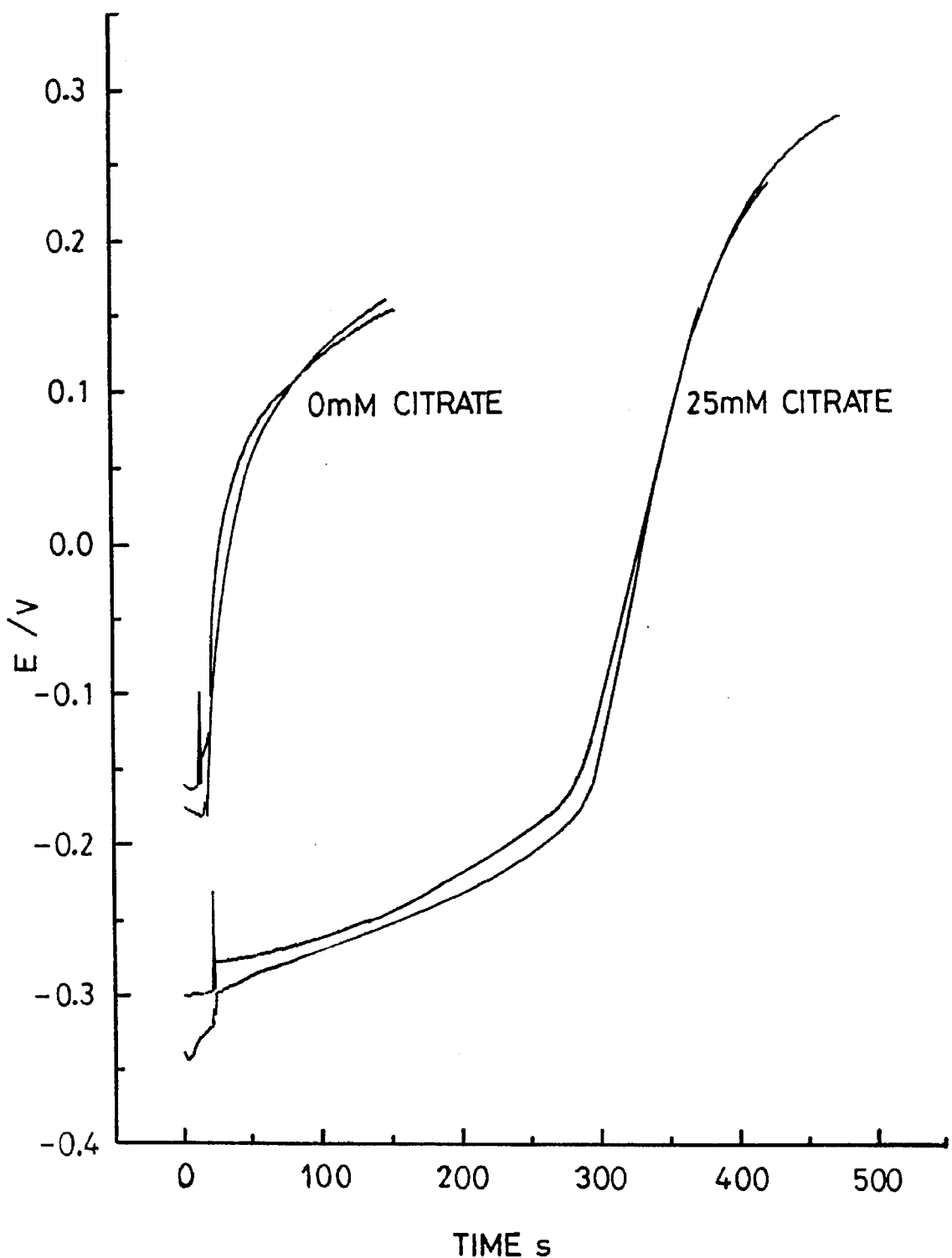
FIG. 3 is a graph of potential (in volts) versus time (in seconds) of results obtained using the device of FIGS. 1 and 2 for test solutions of 25 mM and 0 mM citric acid.

In typical experiments to measure the amount of citric acid in a sample, a constant current of 30 μA is applied between the counter electrode and the generator electrode, and typical results of measurements of redox potential between the sensor and reference electrodes are shown in FIG. 3 for 25 mM citric acid and in the absence of citric acid. A calibration curve comprising points of inflection for different citric acid concentrations with an applied current of 30 μA (approximate current density of 6 AμA $mm^{-2}$) is shown in FIG. 4.

Figure 4:
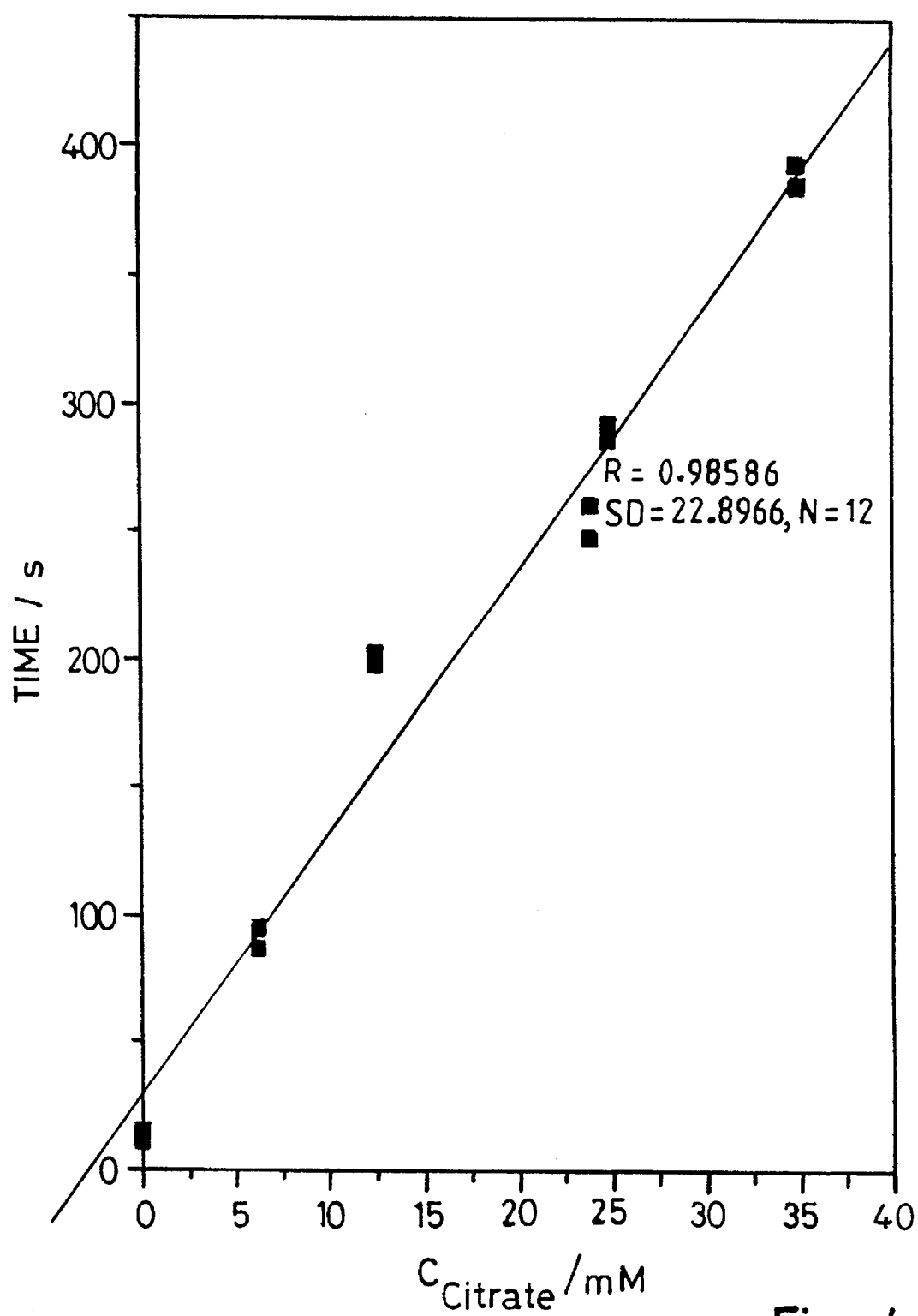
FIG. 4 is a graph of end point time (in seconds) versus citric acid concentration (in mM). The end points are derived from signals including those shown in FIG. 3.

For the experiments producing the data of FIGS. 3 and 4, potassium nitrate was added to the samples to produce a concentration of potassium nitrate of 0.8M. This concentration is higher than is necessary for operation of the device for titration purposes. Typically ionic strength of solution equivalent to between 0.05 and 0.1M is sufficient. However, higher concentrations of potassium nitrate (or other salt) are appropriate when using the device additionally for measuring reducing sugars content as described below.

Instead of applying a constant current, a varying current under suitable software control may be used for improved resolution.

The device of FIGS. 1 and 2 finds particular application in measuring the acid content of fruit juice, e.g. tomato juice, to provide an indication of fruit ripeness. Good results have been obtained using undiluted juice, obtained directly from tomatoes. Such a device may conveniently additionally incorporate further electrodes for measuring reducing sugars content, as described in International Application No. PCT/GB94/02656, with additional electrodes screen printed on plate 10 and located in further compartments similar to compartments 24, 26 and 28. In this case, added salts are generally needed in the device for the sugars determination reaction. An alternative to electrogeneration of hydroxide would be to deposit hydroxide salt such as sodium hydroxide or potassium hydroxide in the relevant compartment. A knowledge of the reducing sugars content of fruit juice provides further information on fruit ripeness and hence readiness for picking.

As noted above, the device may be modified by combining the functions of various electrodes to simplify manufacture and operation.

The counter electrode can additionally function as a reference electrode in place of a separate reference electrode. $H^+$ ions are generated at the counter electrode, consequent on generation of $OH^-$ at the generator electrode. The environment at the counter electrode is initially acid, due to the acid present in the sample under test, so that there is relatively little change in hydrogen ion concentration at the counter electrode compared with the change at the generator electrode where $OH^-$ ions are generated in the acid environment.

Additionally or alternatively, the sensor electrode can be eliminated and the generator electrode used additionally as the sensor electrode by measuring the change in hydrogen ion concentration at the generator electrode within the confines of the compartment containing the generator electrode.

An alternative measurement approach would be to perform a potentiostatic rather than galvanostatic measurement. In this case the potential at the generator electrode with respect to the reference electrode would be held at a defined value for the duration of the test and the potential measured at the sensor electrode through a high impedance circuit as described above. Holding a fixed potential would result in a transient current decay. The end-point would be determined by integrating the current with respect to time and plotting the sensor potential against the integrated current (charge). The point of inflection would be obtained in the normal way, by differentiating with respect to charge rather than time.

We claim:

1. A titration device for measuring the amount of a species in solution in a test liquid, comprising a capillary fill device comprising a generator electrode, a counter electrode, a reference electrode and two parallel spaced-apart plates for receiving a thin layer of test liquid and defining an open ended chamber, the chamber being internally divided by ridges to define at least two side-by-side compartments open at both ends, wherein the ridges do not extend along the full length of the chamber, so that ionic communication between the compartments is permitted, said generator electrode and said counter electrode being located in different compartments.

2. A device according to claim 1 comprising at least three compartments, with the reference electrode located in a different compartment from those in which the counter and generator electrodes are located.

3. A device according to claim 1, wherein the sensor electrode is located in the vicinity of the generator electrode and in the same compartment therewith.

4. A device according to claim 1, wherein the counter and generator electrodes comprise a noble metal.

5. A device according to claim 4, wherein the counter and generator electrodes comprise palladium.

6. A device according to claim 1, wherein the sensor electrode comprises palladium.

7. A device according to claim 1, wherein the reference electrode comprises a silver/silver chloride electrode.

8. A device according to claim 1, wherein the electrodes are formed by a screen printing process.

9. A device according to claim 1, wherein different chemical reagents are located in different compartments.

10. A device according to claim 1, further comprising additional electrodes for measuring the reducing sugars content of a test liquid.

11. A device according to claim 1, wherein a low impedance circuit is set up between the counter electrode and the generator electrode to generate a localized ionic environment in the vicinity of the generator electrode, and a high impedance circuit is set up between the sensor electrode and the reference electrode.

12. A device according to claim 11, wherein test liquid is adapted to be introduced to the chamber and the potential difference between the reference and sensor electrodes is adapted to be measured over time.

\* \* \* \* \*